United States Patent [19]

Brunetta et al.

[11] Patent Number: 5,330,681
[45] Date of Patent: Jul. 19, 1994

[54] STABLE EMULSIONS OF PERFLUOROPOLYETHERS

[75] Inventors: Fabio Brunetta, Treviso; Giovanni Pantini, Milan, both of Italy

[73] Assignee: Ausimont S.r.l., Milan, Italy

[21] Appl. No.: 953,128

[22] Filed: Sep. 29, 1992

Related U.S. Application Data

[62] Division of Ser. No. 501,481, Mar. 30, 1990, Pat. No. 5,183,589.

[30] Foreign Application Priority Data

Mar. 31, 1989 [IT] Italy .................. 19974 A/89

[51] Int. Cl.$^5$ .................. A61K 7/025; A61K 7/40; B01J 13/00
[52] U.S. Cl. .................. 252/312; 252/308; 424/60; 514/845; 514/847; 514/939; 514/941; 514/942
[58] Field of Search .............. 252/308, 312; 514/832, 514/833, 846, 939, 941, 942

[56] References Cited

U.S. PATENT DOCUMENTS

| | | | |
|---|---|---|---|
| 2,808,384 | 10/1957 | Gerbel et al. | 524/317 |
| 3,778,381 | 12/1973 | Rosano et al. | 252/311 |
| 3,823,091 | 7/1974 | Samejima et al. | 252/312 |
| 3,993,581 | 11/1976 | Yokoyama et al. | 252/312 |
| 4,299,728 | 11/1981 | Cormier et al. | 252/312 X |
| 4,395,393 | 7/1983 | Schmolka | 514/832 X |
| 4,510,335 | 4/1985 | Lagow et al. | 252/312 X |
| 4,569,784 | 2/1986 | Moore | 252/312 X |
| 4,742,050 | 5/1988 | Yuhas et al. | 514/34 |
| 4,803,067 | 2/1989 | Brunetta et al. | 514/939 X |
| 4,879,062 | 11/1989 | Moore | 252/312 X |
| 4,990,283 | 2/1991 | Visca et al. | 252/312 X |

OTHER PUBLICATIONS

Abst: 85-084003; JP-143586 (Derwent).
Abst: 85-253804; JP-023797 (Derwent).

*Primary Examiner*—Richard D. Lovering
*Attorney, Agent, or Firm*—Stevens, Davis, Miller & Mosher

[57] ABSTRACT

Stable diphase emulsions consisting of:
a) perfluoropolyethers having perfluoroalkyl end groups;
b) a conventional surfactant, dispersed in
c) a continuous dispersing phase consisting of glycerol or of a polyhydroxylated compound containing at least three hydroxyl groups, selected from polyalcohols and saccharides, dissolved in a hydrophile solvent and/or water.

10 Claims, No Drawings

STABLE EMULSIONS OF PERFLUOROPOLYETHERS

CROSS-REFERENCE TO RELATED APPLICATIONS:

This application is a divisional of application Ser. No. 501,481, filed Mar. 30, 1990, now U.S. Pat. No. 5,183,589.

The present invention relates to stable emulsions of perfluoropolyethers.

In particular, the present invention relates to stable diphase emulsions comprising a liquid perfluoroether component and an organic hydroxylated hydrating and/or wetting agent.

The emulsions forming the object of the present invention are utilized in several known industrial applicative fields for perfluoropolyethers, and in particular in the field of the cosmetic and dermatological specialities and furthermore as so-called premixes in the preparation of the above-said specialities.

The use of perfluoropolyethers as ingredients of various cosmetic and dermatological preparations is known in itself, owing to the possibility of obtaining a protective film on the skin, which film does not represent a hindrance to the physiological functions (such as transpiration, etc.). Nevertheless, difficulties are encountered in the production of cosmetics, which are due to the fact that perfluoropolyethers are in general insoluble in the raw materials utilized in the cosmetic industry, or, at least, it can happen that the performance of the product are jeopardized by a non-homogeneous distribution of the perfluoropolyethers in the cosmetic preparation. In fact, the perfluoropolyethers are fully insoluble in all the organic matters, except in those having a high fluorine content, wherefore the technology has to face the general problem of obtaining dispersions of perfluoropolyethers in organic or aqueous-organic liquids, as the perfluoropolyethers are liquids.

In literature is known the preparation of oil/water emulsions in which the oil consists of a perfluorinated compound. These emulsions have been prepared essentially for the purpose of having available synthetic plasma, utilizing the high solubility of oxygen and carbon dioxide in the perfluorinated compounds which, in such manner, act as oxygen transferors. The utilized perfluorinated compounds belong to the class of the perfluorinated cycloalkanes (preferably having two or more condensed cycles), of the perfluorinated heterocyclic compounds and of the perfluorinated amines. As emulsifiers, the best ones have proven to be the non-ionic emulsifiers and particularly the so-called PLURON/C emulsifiers (which are non-ionic emulsifiers having a chemical structure of polyalkyloxanes and prepared starting from mixtures of ethylene oxide and propylene oxide in a proper ratio). As an alternative, also perfluorinated emulsifiers have been used with the possibility of obtaining emulsions and microemulsions, the uses thereof, however, are limited just by the presence of said surfactants.

This technology has proved to be little suitable for the compounds having the structure of perfluoropolyethers, especially if their molecular weight is higher than 1000. In the preparation of emulsions of the latter, two main difficulties were encountered, which were represented by the choice of an effective emulsifier and by the obtainment of sufficiently stable products.

On the other hand it is known preparing cosmetic three-phase emulsions in which the perfluoropolyether is dispersed in an oil/water or water-oil emulsion or in a cross-linking solid phase suspended in an organic liquid phase.

As far as the Applicant knows, no diphase systems have been described so far, which consist of two liquids, one of which consists of a perfluoropolyether and the other of an organic optionally aqueous substance, in the form of a dispersion of one in the other in order to form a stable emulsion, with the addition of common surfactants, and in particular of non-fluorinated surfactants.

Thus, it is an object of the present invention to provide a diphase emulsion in the form of a fine and homogeneous dispersion of perfluoropolyethers in an organic substance, optionally in the presence of water, which acts as a continuous phase, in the presence of conventional surfactants or emulsifiers.

Another object is that of providing the corresponding method of preparation, while further objects are the compositions containing the abovesaid stable emulsions and the use thereof in the cosmetic and dermatological field.

These and still other objects, which will become more clearly apparent from the following description, are achieved by means of stable emulsions of perfluoropolyether liquids having perfluoroalkyl and groups in a continuous phase of a polyhydroxylated compound selected from glycerol and solutions in hydrophile solvents of polyalcohols, other than glycerol, or saccharides, as better defined hereinafter, in the presence of conventional surfactants. In this way stable, also anhydrous, emulsions are obtained, which are utilizable in the industrial applicative fields which are known for the perfluoropolyethers. In particular, thanks to the film-forming characteristics of the perfluoropolyether component, the emulsions forming the object of the present invention are used in compositions, creams, pastes, pseudo-solid emulsions, and the like, to which they impart the property of forming a transparent, water-repellent and lipo-repellent liquid film, also endowed with permeability to oxygen and other gases, which remains on the surface, on which it is applied, for relatively long stretches of time. The characteristic water- and lipo-repellent properties of the liquid film, make said compositions particularly suitable for appliances in the protective preparations field and for highly effective appliances in the cosmetics and/or dermatological treatments range. In comparison with conventional preparations, those having a water- and lipo-repellent action afford the weighty advantage of keeping a last during effectiveness. In the skin re-hydration treatments it is highly desirable to have available stable, cosmetically acceptable (non-greasy, non-tacky, etc.) compositions, which, besides exhibiting the property of maintaining in the subcutaneous layers such water amounts as are sufficient to retain the elasticity, are also capable of exerting a "barrier" effect towards the outside without, however, adversely affect the skin transpiration. The compositions of the invention, thanks to the perfluoropolyether component contained therein as a stable emulsion, according to the object of the present invention, allow to achieve these objects.

As mentioned hereinbefore, the stable diphase emulsions, forming the object of the present invention, consist of a fine and homogeneous stable dispersion of at least a perfluoropolyether, having perfluoroalkyl end groups, inside a continuous phase of a polyhydroxylated compound selected from glycerol and solutions of polyalcohols or saccharides in hydrophile solvents or water, in the presence of usual surfactants or emulsifiers. The perfluoropolyethers having perfluoroalkyl end groups, i.e. free from functional groups, are well-known compounds, which are described, along with the method for preparing them, in several documents, among which British patent 1,104,482, U.S. Pat. Nos. 3,242,218, 3,665,041, 3,715,378, 4,523,039, European patent applications 148,482, 151,877 and 191,490 and international patent applications WO 87/00538 and WO 37/02992.

Suitable perfluoropolyethers are, for example, the ones characterized by the presence of one or more repeating perfluoro-oxyalkylene units a) $(CF_2-CF_2O)$ b) $(CF_2O)$ c) $(C_3F_6O)$, simplified formula for $(CF_2-CF-O)$
$\qquad\qquad\qquad\qquad\qquad\qquad\quad\;\;|$
$\qquad\qquad\qquad\qquad\qquad\qquad\;\;CF_3$ d) $(CF_2O-CF_2-CF_2O)$ e) $(CF_2-CF_2-CF_2O)$ f) (CFO)
$\;\;\;|$
$\;CF_3$ g) 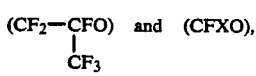

wherein groups $R_f'''$, like or different from one another, are a fluorine atom or a perfluoroalkyl group.

Preferably the perfluoropolyethers suitable for the present invention exhibit the following individual perfluoro-oxyalkylene units or the following combinations of perfluoro-oxyalkylene units:

I) $(CF_2-CF_2O)$ and $(CF_2O)$, said units being statistically distributed along the perfluoropolyether chain; or

II)

$(CF_2-CFO)$ and (CFXO),
$\quad\;\;\;|$
$\;\;\;\;CF_3$ wherein X is F or $CF_3$, said units being statistically distributed along the chain; or

III)

$(CF_2-CF_2O)$, $(CF_2-CFO)$ and (CFXO)
$\qquad\qquad\qquad\quad\;\;|$
$\qquad\qquad\qquad\;CF_3$ in which X is F or $CF_3$, said units being statistically distributed along the chain; or

IV)

$(CF-CF_2O)$;
$\;|$
$CF_3$ or

V) $(CF_2-CF_2-CF_2O)$; or

VI) $(CF_2-CF_2O)$; or

VII)

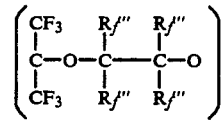

wherein groups $R_f'''$, like or different from one another, are a fluorine atom or a perfluoroalkyl group; or

VIII) $(CF_2O-CF_2-CF_2O)$.

Suitable perfluoropolyethers are also the ones which contain perfluorooxetane rings

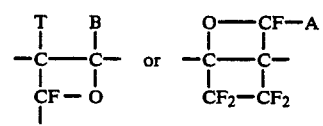

in which T, B and R, like or different from one another, are perfluoro-oxyalkyl, perfluoropolyoxyalkyl or perfluoroalkyl radicals and A is a perfluorooxyalkyl, perfluoropolyoxyalkyl or perfluoroalkyl radical.

Examples of suitable perfluoropolyethers having repeating perfluorooxyalkylene units are the ones belonging to the following classes:

A)

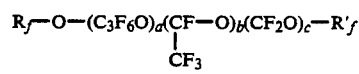

wherein: $R_f$ and $R'_f$, like or different from each other, are selected from the group consisting of $CF_3$, $C_2F_5$ and $C_3F_7$: units $C_3F_6O$ (oxytrifluoromethyltrifluoroethylene),

and $CF_2-O$ are statistically distributed along the chain; a is an integer; b and c are integers or zero; when the sum (b+c) is other than zero, the

ratio ranges from 5 to 40;

B) $CF_3O-(C_2F_4O)_d(CF_2O)_e-CF_3$ wherein units $C_2F_4O$ and $CF_2O$ are statistically distributed along the chain; d and e are integers; the d/e ratio ranging from 0.3 to 5;

C) $CF_3O-(C_3F_6O)_f(C_2F_4O)_g(CFXO)_h-CF_3$ wherein units $C_3F_6O$, $C_2F_4O$ and CFXO are statistically distributed along the chain; X is F or CF$_3$; f, g and h are integers; the $$\frac{f}{g+h}$$

ratio varies from 1 to 50, and the g/h ratio varies from 1 to 10;

D) R$^3$O—(CF$_2$CF$_2$CF$_2$O)$_j$R$^4$, wherein R$^3$ and R$^4$, like or different from each other, are —CF$_3$ or —C$_2$F$_5$ and j is an integer.

The perfluoropolyethers suited to be used in the present invention have usually a number average molecular weight ranging from 500 to 20,000 and, more usually, from 1,000 to 10,000.

As already mentioned above, the perfluoropolyethers according to the present invention are dispersed in emulsion inside a continuous phase of a polyhydroxylated compound selected from glycerol as such and polyalcohols and saccharides in concentrated solution in a hydrophile solvent or water, containing at least three hydroxyl groups, preferably in the absence of hydrogenated carbon atoms.

As regards glycerol, it is the preferred compound and it can be used just as if it is available in commerce, generally containing up to 5% of water.

Any polyalcohol can be utilized on the only condition that it should be liquid in ambient conditions or that it should be soluble in the hydrophile solvent or in water until obtainment of concentrated solutions.

Suitable polyalcohols are for example the ones which contain from 3 to 12 carbon atoms with at least 3 hydroxyl groups other than glycerol. In like manner, under the same conditions of solubility in the hydrophile solvent it is possible to use the saccharides (from mono- to tri-saccharides) C$_4$-C$_{18}$ and/or mixtures thereof like the ones obtainable from the hydrolytic demolition of polysaccharides such as cellulose and starch.

Suitable hydrophile solvents are, for example, glycols, glycerol itself, lower alcohols, ethereal solvents, diglymes etc., also if aqueous.

However, it is usually operated with water.

The hydrophile solvent is used in the lowest amount sufficient to obtain a concentrated solution (syrup) of the polyalcohol or saccharide compound.

However, the concentrated aqueous solutions (syrups) of polyalcohols and saccharides (sugars) available on the market are utilizable.

The concentration of the solutions usually amounts to a value ranging from 50% to 80% by weight. Glycerol is used as such because it is already in the liquid state.

The following polyalcohols and saccharides have proved to be particularly effective: glycerol, xylitol, mannitol, sorbitol, glucose, fructose, saccharose, maltitol, dimer compounds of glycerol (di-glycerol or bis(2,3-di-hydroxypropyl) ether, solid water soluble polyhydroxylated compounds as sugars and glycerol condensation products as triglycerol and tetraglycerol.

These are known compounds which are in the form of crystalline powders soluble both in water and in hydroxylated solvents.

The dispersion in emulsion is carried out, last, in the presence of conventional surfactants, preferably of the cosmetic type. The surfactants of the cationic, anionic, amphoteric and non-ionic type have proved to be useful compounds, the preferred ones being those of the ionic type.

Among the others, the following ones have proved to be effective:

sodium lauryl sulphate (solution at 28%) Texapon N40 (Henkel), sulphosuccinate (sulphosuccinic hemiester) (solution at 30%) Texapon SB 3 (Henkel), coco-amphocarboxyglycinate (solution at 40%) Dehyton D (Henkel), potassium cetyl phosphate (solid product) Amphisol K (Givaudan), sodium alkyl-polyoxyethylene-ether carboxylate Nikkol ECTD-3NEX (Nikko Chemicals), potassium benzalconium chloride (solution at 50%) (purchased from trade company Res Pharma), alkyl amidopropyl betaine (solution at 40%) Dehyton K (Henkel).

As already mentioned, sufficiently stable emulsions have been prepared also with non-ionic emulsifiers such as:

cetyl-stearilic ethoxylated alcohol Emulgin B1 (Henkel), sorbitan-ethoxylate(20)-mono-oleate Tween 20 (ICI Speciality Chemicals).

The quantitative ratios of the components of the stable emulsion according to the present invention can be defined as follows:

1. In the case of using glycerol as the continuous phase:
   a) perfluoropolyether: from 0.01% to 99.9%, preferably from 0.1% to 75%, by weight referred to the total weight of the emulsion;
   b) surfactant: from 0.01% to 30%, preferably from 0.01% to 5%, by weight referred to the total weight of the emulsion and at any rate the lowest possible amount;
   c) glycerol: the balance to 100% by weight.

2. In the case of using polyalcohols or saccharides (in the solid state) dissolved in the least hydrophile solvent amount necessary to obtain a concentrated solution (syrup in H$_2$O):
   a) perfluoropolyether: from 0.01% to 80%, preferably from 0.01% to 50%, by weight referred to the total weight of the emulsion;
   b) surfactant: from 0.01% to 30%, preferably from 0.01% to 5%, by weight referred to the total weight of the emulsion;
   c) polyhydroxylated compound (polyalcohol or saccharide) expressed at 100% in the form of concentrated solution in the hydrophile solvent: the balance to 100%.

In the limits of the preferred percent composition it is possible to obtain emulsion of the Newtonian type with particles of the order of 0.5-0.8 microns.

The emulsions of the present invention are prepared by adding a perfluoropolyether to a solution of a preferably ionic surfactant or emulsifier, as defined hereinbefore, in glycerol or in the polyalcohol or saccharide in concentrated solution (syrup in H$_2$O) in the above-specified ratios, maintaining the system under stirring, for example by means of a turboemulsifier Silverson L/2R at room temperature.

As already mentioned, the emulsions of the invention exhibit remarkable film-forming effects: the obtained liquid film is transparent and permeable to gases. A significant proof of the waterproof effect is provided by applicating a cream according to the invention on the hands and then by washing the hands. After washing, water glides away leaving the skin dry.

Thanks to the above-mentioned properties, the emulsions of the invention are particularly suitable for applications in the field of cosmetology and dermatology.

Examples of these applications are:

a) as barrier creams and other protecting preparations (hand creams, ointments or pastes to prevent contact irritations and dermatitis; creams against dermatitis caused by household or work surfactants);

b) in the paedo-cosmetology as protective creams or pastes for children;

c) in the sun products to prolong the action thereof;

d) as anti-wrinkle products and for the decorative cosmetology, for example in products such as make-up foundation products, eyeshadows and the like. In this case, the presence of the fluorinated compound promotes the flowability and therefore facilitates the spreadability of the products, thereby preventing or minimizing antiaesthetic caking of the product on the skin; in lipsticks and lipglosses, for example, an improvement of both flowability and gloss is obtained;

e) as creams for massages; since the fluorinated compound is not absorbed by the skin, it permits also prolonged massages, thereby allowing the penetration of "active matters", if any;

f) in dermatological applications, as a vehicle for the medicaments.

The percent amount of perfluoropolyether in the cosmetic emulsions varies as a function of the type of end use of the number of daily applications and of the application time. Said amount generally ranges from 0.2–0.5% for the antiwrinkle creams to be utilized every day, up to 3–5% for highly protective creams. The persistence of the perfluoropolyether on the skin is rather long: the elimination occurs either by washing or by diffusion on the clothes of by natural desquamation of the skin.

The following examples are given for illustrative purposes and are not to be considered as a limitation of the invention. Unless otherwise specified, all the parts are parts by weight.

Furthermore, the parts of polyalcohols or of saccharides and of surfactant are indicated as such according to the indicated concentration.

The following perfluoropolyethers have been used:

Fomblin HC/25 (Montefluos S.p.A.), (number average molecular weight) M.W.=3200; kinematic viscosity=250 cSt (20° C.);

Fomblin HC/R (Montefluos S.p.A.), M.W.=6600; kinematic viscosity=1500 cSt (20° C.);

Galden D 03 (Montefluos S.p.A.), M.W.=870; kinematic viscosity=2.4 cSt (25° C.);

Galden D 10 (Hontefluos S.p.A.), M.W.=1320; kinematic viscosity=9 cSt (25° C.), all of them having the chemical structure:

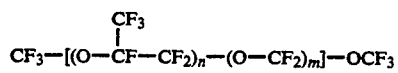

wherein n/m=20-40.

Fomblin Z/25 (Montefluos S.p.A.), M.W.=9400; kinematic viscosity=255 cSt (20° C.), having chemical structure:

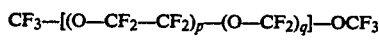

wherein p/q=0.6–0.7.

Fomblin M30 (Montefluos S.p.A.), M.W.=9400; kinematic viscosity=310 cSt (20° C.), having chemical structure like the one of Fomblin Z/25 with p/q=1.2.

Krytox 1525 (Du Pont), M.W.=4600; kinematic viscosity=261 cSt (20° C.), having chemical structure:

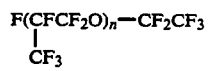

wherein n=25-30.

Demnum S-100 (Daikin), M.W.=5600; kinematic viscosity=250 cSt (20° C.), having chemical structure:

wherein n=30-35.

These is dealt with trade names.

The stability was measured on the individual emulsions prepared in a centrifuge operating at 4000 r.p.m., during 1 hour, and then subjected to an ageing test at room temperature during 3 months on a shelf, then in an oven at 100° C. during 1 week and at 180° C. during 3 hours.

EXAMPLE 1

An emulsion was prepared by stirring in a Silverson L/2R turbo emulsifier at 5000/6000 r.p.m. 20 parts of perfluoropolyether Fomblin HC/25 in 80 parts of glycerol, in the presence of 2 parts of emulsifying surfactant Texapon N40, solution at 28%. It was operated as follows: the emulsifier was dissolved in glycerol and then the perfluoropolyether was added while stirring at room temperature for a few instants. An emulsion was obtained, which, subjected to the above-described stability tests, proved to be stable.

EXAMPLES 2-5

Example 1 was repeated under the same conditions and with the same ingredients, but varying the amounts in the formulation as is indicated in the following Table 1 along with the results.

TABLE 1

| Example | Glycerol (parts) | Fomblin HC/25 (parts) | Stability |
|---------|------------------|----------------------|-----------|
| 2 | 90 | 10 | yes |
| 3 | 50 | 50 | " |
| 4 | 30 | 70 | " |
| 5 | 25 | 75 | " |

EXAMPLES 6-11

Examples 1 to 6 were repeated, but substituting Fomblin HC/R for Fomblin HC/25, thereby obtaining the results reported in the following Table 2.

TABLE 2

| Example | Glycerol (parts) | Fomblin HC/R (parts) | Stability |
|---------|------------------|----------------------|-----------|
| 6 | 90 | 10 | yes |
| 7 | 80 | 20 | " |
| 8 | 70 | 30 | " |
| 9 | 50 | 50 | " |
| 10 | 30 | 70 | " |
| 11 | 25 | 75 | " |

EXAMPLES 12-16

It was operated as is described in example 2, but varying the emulsifier amount as indicated in Table 3.

TABLE 3

| Example | Glycerol (parts) | Fomblin HC/25 (parts) | Texapon N40 (parts) |
|---|---|---|---|
| 12 | 90 | 10 | 0.5 |
| 13 | " | " | 0.25 |
| 14 | " | " | 0.10 |
| 15 | " | " | 0.05 |
| 16 | " | " | 0.025 |

Stable emulsions were obtained.

EXAMPLES 17-20

It was operated as in example 1, but glycerol was substituted by the following polyhydroxylated compounds (polyols or saccharides) in aqueous solution, according to the formulations indicated in Table 4.

TABLE 4

| Example | Polyhydroxylated compound (parts) | Fomblin HC/25 (parts) | Texapon N40 (parts) |
|---|---|---|---|
| 17 | Maltitol (solution at 74%) | 90 | 10 | 0.025 |
| 18 | Sorbitol (solution at 70%) | 90 | 10 | 2 |
| 19 | Glucose (solution at 70%) | 90 | 10 | 2 |
| 20 | Saccharose (solution at 70%) | 90 | 10 | 2 |

The emulsions obtained were stable. Analogous results were obtained when using xylitol and mannitol syrups.

EXAMPLES 21-23

Example 1 was repeated, substituting other ionic emulsifiers for Texapon N40, according to the formulations indicated in Table 5.

TABLE 5

| Example | Glycerol (parts) | Fomblin HC/25 (parts) | Emulsifier (parts) | |
|---|---|---|---|---|
| 21 | 90 | 10 | Amphisol K (solid) | 0.25 |
| 22 | 80 | 20 | Nikkol ECTD-3NEX (semisolid) | 1 |
| 23 | 90 | 10 | Benzalconium chloride K (solution at 50%) | 25 |

Stable emulsions were obtained. Analogous results were obtained when using the following ionic surfactants: Dehyton D; Texapon 5B3 and Dehyton K.

EXAMPLE 24

Example 1 was repeated using the following formulation:

| Maltitol (solution at 74%) | 40 parts |
|---|---|
| Fomblin HC/25 | 20 parts |
| Dehyton K (solution at 40%) | 2 parts |

A stable emulsion was obtained.

EXAMPLES 25-26

Example 1 was repeated using the following formulations comprising a non-ionic emulsifier, according to Table 6.

TABLE 6

| Example | Glycerol (parts) | Fomblin HC/25 (parts) | Emulsifier (parts) | |
|---|---|---|---|---|
| 25 | 90 | 10 | Tween 20 | 1 |
| 26 | 90 | 10 | Emulgin B1 | 2 |

Shelf-stable emulsions were obtained.

EXAMPLES 27-32

Example 1 was repeated but substituting other perfluoropolyethers for Fomblin HC/25, according to the formulations indicated in Table 7.

TABLE 7

| Example | Glycerol (parts) | Texapon N40 (parts) | Perfluoropolyether (parts) | |
|---|---|---|---|---|
| 27 | 90 | 2 | Demnum S/100 | 2 |
| 28 | 90 | 2 | Krytox 1525 | 10 |
| 29 | 90 | 1 | Galden D03 | 18 |
| 30 | 74 | 1 | Galden D10 | 25 |
| 31 | 90 | 2 | Fomblin Z/25 | 10 |
| 32 | 90 | 2 | Fomblin 30M | 10 |

Stable emulsions were obtained.

EXAMPLES 33-36

It was operated as in example 1, according to the formulations indicated in Table 8.

TABLE 8

| Example | Glycerol (parts) | Fomblin HC/25 (parts) | Texapon N40 (parts) |
|---|---|---|---|
| 33 | 38 | 60 | 2 |
| 34 | 36 | 62 | 2 |
| 35 | 34 | 64 | 2 |
| 36 | 32 | 64 | 4 |

Stable emulsions were obtained.

EXAMPLE 37

It was operated as in example 1, according to the following formulation:

| Maltitol | 58 parts |
|---|---|
| Fomblin HC/25 | 40 parts |
| Texapon N40 (solution at 28%). | 2 parts |

A stable emulsion was obtained.

EXAMPLE 38

It was operated as in example 1, according to the following formulation:

| di-glycerol | 70 parts |
|---|---|
| Fomblin HC/R | 28 parts |
| Texapon N40 | 2 parts |

A stable emulsion was obtained.

EXAMPLE 39

It was operated as in Example 1, according to the following formulation:

| glycerol | 50 parts |
|---|---|
| propylene glycol | 28 parts |
| Fomblin HC/25 | 20 parts |
| Texapon N40 | 2 parts |

A stable emulsion was obtained.

EXAMPLE 40

Preparation of creams according to the perfluoropolyether pre-emulsification technology

| Hydrating cream | (% by weight) |
|---|---|
| a) PEG-8 $C_{12-18}$ alkyl ester | 6.0 |
| PEG-20 methyl-glucose sesquistearate | 1.2 |
| Isopropyl stearate | 5.0 |
| Cetyl alcohol | 3.0 |
| Stearic acid | 1.0 |
| Octyl stearate | 6.0 |
| Almond oil | 2.0 |
| Antioxidants | as sufficient |
| b) Water, balance to | 100.0 |
| Natural hydrating factors | 1.0 |
| c) Emulsion (example 1) | 4.0 |
| d) Perfume, preserving agents and sequestering agents | as sufficient |

Procedure

The emulsion of Fowblin HC/25 in glycerol, as specified in example 1,(c), was utilized. a) and b) were separately heated to 75° C. b) was added to a) under stirring.

Emulsion c) was added at room temperature, stirring was carried on and d) was added.

A centrifugation-stable cream was obtained, in which Fomblin HC/25 was present in a finely dispersed form (below 1 micron).

EXAMPLE 41

| Sun emulsion | (% by weight) |
|---|---|
| a) Stearic acid | 4.0 |
| Cetyl alcohol | 1.0 |
| Caprylic acid/capric acid esterified with coco alcohol | 6.0 |
| Tocopherol acetate | 2.5 |
| Dimethicone | 0.3 |
| Octyl methoxycinnamate | 6.0 |
| Butylmethoxybenzoyl methane | 1.5 |
| b) Potassium cetyl phosphate (Amphisol K) | 2.0 |
| c) Potassium hydroxide | 0.15 |
| Pantenol (aminoalcohol) | 2.0 |
| d) Gelling agent (acrylic polymer: Carbomer 940) | as sufficient |
| Water, balance to | 100.0 |
| e) Emulsion (example 1) | 7.0 |
| f) Perfume, sequestering agents and preserving agents | as sufficient |

Procedure a) was heated to 85° C. in a (planetary type) mixer, then b) was added. After a homogeneous solution was obtained, c), preheated to 75° C., was added and mixing was continued. The whole was allowed to cool to 40° C. d) was added.

The emulsion of Fomblin HC/25 in glycerol, as specified in example 1 (e), was utilized.

e) was added under stirring until reaching the room temperature, f) was then added.

EXAMPLE 42

| Barrier Cream | (% by weight) |
|---|---|
| a) PEG-8 $C_{12-18}$ alkyl ester | 10.0 |
| Glyceryl stearate and PEG-100 stearate | 3.0 |
| Octyl stearate | 10.0 |
| Cetyl alcohol | 3.0 |
| b) Water, balance to | 100.0 |
| c) Emulsion (example 9) | 6.0 |
| d) Perfume, preserving agents and sequestering agents | as sufficient |

Procedure

The emulsion of Fomblin HC/R in glycerol, as specified in example 9 (c), was utilized.

a) and b) were heated separately to 75° C. b) was added to a) under stirring.

At room temperature (for indifferently also in hot conditions) emulsion c) was added. Stirring was carried on and d) was added.

EXAMPLE 43

| Antiwrinkle cream based on retinol | (% by weight) |
|---|---|
| a) Cetylstearylic alcohol 12 OE | 1.5 |
| Cetylstearylic alcohol 20 PE | 1.5 |
| Stearic acid mono-diglyceride | 10.0 |
| Cetylstearylic alcohol | 2.0 |
| Caprylic/capric acids triglycerine Acetylstearyl isononanoate | 5.0 |
| Silicone oil 350 cps | 0.5 |
| Retinol palmitate 1,000,000 UI/ml | 1.0 |
| Antioxidants | as sufficient |
| b) Water, balance to | 100.0 |
| c) Emulsion (example 1) | 7.0 |
| d) Perfume, preserving agents and sequestering agents | as sufficient |

Procedure

The aqueous phase and the oily phase were heated separately to 75° C., emulsifying them by means of a turbine and cooling them under stirring. The thermolabile components, the Fomblin emulsion and the perfume were added at 40° C., and mixing was carried on until reaching the room temperature.

We claim:

1. Stable emulsions of perfluoropolyethers having perfluoroalkyl end groups, consisting of:
    a) from 0.01% to 50% by weight of a perfluoropolyether;
    b) from 0.01% to 5% of a surfactant; and
    c) from 45 to 99.98% of a solution in water of a polyhydroxylated compound selected from the group consisting of polyalcohols other than glycerine and the saccharides containing at least three hydroxylic groups;
        i) said solution in water is a syrup (a concentrated solution) containing 50 to 80% by weight of the polyhydroxylated compound;
        ii) the polyhydroxylated compounds are crystalline powders soluble in water;
        iii) the surfactant is an ionic surfactant or emulsifier used for cosmetics.

2. The emulsions according to claim 1, wherein the perfluoropolyether is selected from the group consisting of perfluoropolyethers containing one or more of the following repeating perfluorooxyalkylene units:

a) $(CF_2-CF_2O)$;

b) $(CF_2O)$;

c) $(CF_2-CF-O)$;
        $\phantom{(CF_2-}|$
        $\phantom{(CF_2-}CF_3$ d) $(CF_2O-CF_2-CF_2O)$;

e) $(CF_2-CF_2-CF_2O)$;

f) $(CFO)$; and
   $\phantom{(}|$
   $\phantom{(}CF_3$ g) 
$$\begin{array}{ccc}
CF_3 & R_f''' & R_f''' \\
| & | & | \\
(C-O-C & -C-O) \\
| & | & | \\
CF_3 & R_f''' & R_f'''
\end{array}$$

wherein the group $R_f'''$ are alike or different, and are a fluorine atom or a perfluoroalkyl group.

3. The emulsions according to claim 1, wherein the perfluoropolyether is selected from the group consisting of perfluoropolyethers containing the following perfluorooxyalkylene units either singly or combined with one another:

I) $(CF_2-CF_2O)$ and $(CF_2O)$, said units being statistically distributed along the perfluoropolyether chain;

II)
$(CF_2-CFO)$ and $(CFXO)$,
$\phantom{(CF_2-}|$
$\phantom{(CF_2-}CF_3$ wherein X is F or $CF_3$, said units being statistically distributed along the chain;

III)
$(CF_2-CF_2O)$, $(CF_2-CFO)$ and $(CFXO)$
$\phantom{(CF_2-CF_2O), (CF_2-}|$
$\phantom{(CF_2-CF_2O), (CF_2-}CF_3$ wherein X is F or $CF_3$, said units being statistically distributed along the chain;

IV)
$(CF-CF_2O)$;
$|$
$CF_3$

V) $(CF_2-CF_2-CF_2O)$;
VI) $(CF_2-CF_2O)$; and
VII)

$$\begin{array}{ccc}
CF_3 & R_f''' & R_f''' \\
| & | & | \\
(C-O-C & -C-O) \\
| & | & | \\
CF_3 & R_f''' & R_f'''
\end{array}$$

wherein groups $R_f'''$ are the same or different, and represent a fluorine atom or a perfluoroalkyl group; and

VIII) $(CF_2O-CF_2-CF_2-O)$.

4. The emulsions according to claim 1, wherein the perfluoropolyether is selected from the group consisting of perfluoropolyethers containing perfluorooxetane rings of the formula:

$$\begin{array}{cc}
T \quad B & O\text{---}CF\text{---}A \\
| \quad | & | \quad\quad | \\
-C\text{---}C- \text{ and } -C\text{---}C- \\
| \quad | & | \quad\quad | \\
CF\text{---}O & CF_2\text{---}CF_2 \\
| & \\
R &
\end{array}$$

wherein T, B and R are the same or different from one another, and are selected from the group consisting of a perfluorooxyalkyl, perfluoropolyoxyalkyl and perfluoroalkyl radicals and A is selected from the group consisting of a perfluorooxyalkyl, perfluoropolyoxyalkyl and a perfluoroalkyl radical.

5. The emulsion according to claim 1, wherein the perfluoropolyether is selected from the group consisting of
A)

$R_f-O-(C_3F_6O)_a(CF-O)_b-(CF_2O)_c-R'_f$
$\phantom{R_f-O-(C_3F_6O)_a(}|$
$\phantom{R_f-O-(C_3F_6O)_a(}CF_3$ wherein $R_f$ and $R_f'$ are alike or different, and are selected from the group consisting of $CF_3$, $C_2F_5$ and $C_3F_7$; units $C_3F_6O$ (oxytrifluoromethyltrifluoroethylene)

$CF-O$
$|$
$CF_3$ and $CF_2$-O being statistically distributed along the chain; a) is an integer; b) and c) are integers or zero; when the sum of b+c is other than zero, then the ratio a/b+c is from 5 to 40;

B) $CF_3O-(C_2F_4O)_d(CF_2O)_e-CF_3$
wherein units $C_2F_4O$ and $CF_2O$ are statistically distributed along the chain; d and e are integers; and the ratio d/e is from 0.3 to 5;

C) $CF_3O-(C_3F_6O)_f(C_2F_4O)_g(CFXO)_h-CF_3$
wherein units $C_3F_6O$, $C_2F_4O$ and CFXO are statistically distributed along the chain; X is F or $CF_3$, f, g and h are integers, the ratio f/g+h is from 1 to 50, and the ratio g/h is from 1 to 10;

D) $R^3_fO-(CF_2CF_2CF_2O)_jR^4_f$
wherein $R^3_f$ and $R^4_f$ are alike or different and are $-CF_3$ or $-C_2F_5$ and j is an integer.

6. The emulsion according to claim 1, wherein the perfluoropolyether has a number average molecular weight ranging from 500 to 20,000.

7. The emulsions according to claim 1, wherein the perfluoropolyether has a number average molecular weight ranging from 1,000 to 10,000.

8. The emulsion according to claim 1, wherein the polyalcohols other than glycerine are selected from the group consisting of polyalcohols containing from 3 to 12 carbon atoms and the saccharides are obtained from the hydrolytic demolition of polysaccharides and contain from 4 to 18 carbons and mixtures thereof.

9. The emulsions according to claim 1, wherein the polyhydroxylated compound is selected from the group consisting of xylitol, mannitol, sorbitol, glucose, maltitol, saccharose, fructose, di-glycerol, triglycerol and tetraglycerol.

10. The emulsion according to claim 1, wherein the surfactant is selected from the group consisting of cationic, anionic and amphoteric emulsifiers.

* * * * *